US008796336B2

(12) United States Patent
Schellenberg et al.

(10) Patent No.: US 8,796,336 B2
(45) Date of Patent: Aug. 5, 2014

(54) METHOXYPOLYETHYLENE GLYCOL CHELATE AND USES THEREOF

(75) Inventors: Karl A. Schellenberg, Virginia Beach, VA (US); Frank A. Lattanzio, Chesapeake, VA (US); James Shaeffer, Wytheville, VA (US)

(73) Assignee: Eastern Virginia Medical School, Norfolk, VA (US)

( * ) Notice: Subject to any disclaimer, the term of this patent is extended or adjusted under 35 U.S.C. 154(b) by 219 days.

(21) Appl. No.: 13/188,914

(22) Filed: Jul. 22, 2011

(65) Prior Publication Data

US 2012/0016030 A1 Jan. 19, 2012

Related U.S. Application Data

(63) Continuation of application No. 12/279,521, filed as application No. PCT/US2007/003682 on Feb. 14, 2007, now Pat. No. 8,008,347.

(60) Provisional application No. 60/772,874, filed on Feb. 14, 2006.

(51) Int. Cl.
*A61L 27/54* (2006.01)
*A61K 31/225* (2006.01)
*C07C 229/26* (2006.01)

(52) U.S. Cl.
USPC .......................................... 514/564; 562/553

(58) Field of Classification Search
USPC .......................................... 514/564; 562/553
See application file for complete search history.

(56) References Cited

U.S. PATENT DOCUMENTS 6,020,373 A * 2/2000 Schellenberg et al. ....... 514/547
7,388,028 B2 6/2008 Schellenberg et al.

FOREIGN PATENT DOCUMENTS

WO WO2004/058289 * 7/2004 ............. A61K 38/00

OTHER PUBLICATIONS

Kuehn et al. Retinal Ganglion Cell Death in Glaucoma: Mechanisms and Neuroprotective Strategies, Ophthalmol. Clin. N. Am. 18, 383-395 (2005).*
Ayene et al., "Radioprotective effect of 2-mercaptopropionylglycine on radiation-induced microsomal lipid peroxidation," Int. J. Radiat. Biol., 48(2): 197-205 (1985) (9 pages).
Beebe et al., "Diverse effects of manosecond pulsed electric fields on cells and tissues," DNA and Cell Biology, 22(12): 785-796 (2003) (12 pages).
Beebe et al., "Nanosecond pulsed electric fields modulate cell function through intracellular signal transduction mechanisms," Physiol. Meas., 25: 1077-1093 (2004) (17 pages).
Blijenbert et al., "A simple method for the determination of EDTA in serum and urine," Clin. Chim. Acta 26: 577-579 (1969) (3 pages).
Buckmann et al., "Preparation of technical grade polyethylene glycol (PEG) (M.sub.r20,000)- N.sup.6-(2- Aminoethyl)-NADH by a procedure adaptable to large-scale synthesis," Biotech. and Appl. Biochem., 9: 258-268 (1987) (12 pages).
Chen et al., "Leukemic cell intracellular responses to nanosecond electric fields," Biochem. and Biophys. Res. Commun., 317(2):421-427 (2004) (7 pages).
Clifton et al., "Effect of D, .alpha.-Tocopheryl succinate and polyethylene glycol on performance tests after gluid percussion brain injury," J. of Neurotrauma, 6: 71-81 (Nov. 2, 1989) (11 pages).
Copy of Extended Search Report and Written Opinion dated Feb. 15, 2012 for corresponding European Patent Application No. 11181006.5 (8 pages).
Dreyer et al., "Elevated glutamate levels in the vitreous body of humans and monkeys with glaucoma," Arch. Ophthalmol., 114: 299-305 (1996) (7 pages).
Duewell et al., "Nonionic polyethylene glycol-ferrioxamine as a renal magnetic resonance contrast agent," Invest. Radiol., 26(1): 50-57 (1991) (8 pages).
European Patent Application No. 07750513 Supplementary Search Report (search completed Sep. 17, 2010) (2 pages).
Fabrizio Carta et al., "Novel therapies for glaucoma: a patent review 2007-2011," Expert Opin. Ther. Patents, vol. 22, No. 1, Jan. 1, 2012, pp. 79-88.
Gais, "Synthesis of thiol and selenol esters from carboxylic acids and thiols or selenols, respectively," Angew. Chem. Int. Ed. Eng., 16: 244-246 (1977) (3 pages).
Hirschelmann et al, Biomed. Biochem Acta, Action of Metal Chelators on Lipoxygenases, Cyclooxygenase and on Inflammation-inducedVassodepression, 1988, 47 (10-11): S256-259, Abstract.
Hoesktra et al., "Mechanism of fusion of sendai virus: role of hydrophobic interactions and mobility constraints of viral membrane proteins," J. of Biol. Chem., 264(12): 6786-6792 (1989) (7 pages).
Lattanzio, Jr. et al., "Cocaine increases intracellular calcium and reactive oxygen species, depolarizes mitochondria, and activates genes associated with heart failure and remodeling," Cardiovascular Toxicology, 05: 377-389 (2005) (15 pages).
Nickells, "Retinal ganglion cell death in glaucoma: the how, the why, and the maybe," Journal of Glaucoma, 5: 345-356 (1996) (12 pages).
PCT/US2007/003682 International Search Report, mailed Feb. 22, 2008 (2 pages).

(Continued)

*Primary Examiner* — Johann R Richter
*Assistant Examiner* — Mark Luderer
(74) *Attorney, Agent, or Firm* — Wilmer Cutler Pickering Hale and Dorr LLP

(57) ABSTRACT

The present invention is directed generally to protecting cells, tissues and organs against the damaging effects of ionizing or other damaging agents associated with radiation or chemotherapy, or degenerative diseases or processes of various organs that elicit the production of free radicals or oxidants such as peroxides, superoxide anions, hydroxyl radicals or nitric oxides, or heavy metal cations. More particularly, the present invention is concerned with methoxypolyethylene glycol chelate methyl esters that are useful as protectors against tissue damage by penetrating the cell membrane to donate electrons to free radical oxidants and remove heavy metals that may react with peroxides to produce the reactive hydroxyl radical, or remove $Ca^{++}$ that may be released from organelles. These chelate esters will also have utility in reducing intraocular pressure in glaucoma patients.

8 Claims, 12 Drawing Sheets

(56) References Cited

OTHER PUBLICATIONS

Riddles et al., "Reassessment of Ellman's Reagent," Methods in Enzymology, 91: 49-60 (1983) (12 pages).

Samudre et al. "Comparison of topical steroids for acute anterior uveitis," J. of Ocular Pharm. and Therap., 20(6): 533-547 (2004) (15 pages).

Schoenbach et al., "Ultrashort electrical pulses open a new gateway into biological cells," Proceedings of the IEEE, 92(7): 1122-1137 (Jul. 2004) (16 pages).

Shaeffer et al., "Polyethylene glycol as a protector against head and neck irradiation," Int. J. Radiat. Oncol. Biol. Phys., 10(12): 2329-2333 (1984) (5 pages).

Shaeffer et al., "Radioprotective effect of polyethylene glycol," Radiation Research, 107: 125-135 (1986) (11 pages).

Vos et al., "Radioprotection by glutathione esters and cysteamine in normal and glutathione-depleted mammalian cells," Int. J. Radiat. Biol., 53(2): 273-281 (1988) (9 pages).

Wasserman, "Radiotherapeutic studies With Amifostine (Ethyol)," Seminars in Oncology, 21(5): 21-25 (1994) (5 pages).

Wuenschell et al., "Chiral copper-chelate complexes alter selectivities in metal affinity protein partitioning," J. of Chrom., 543: 345-354 (1991) (10 pages).

\* cited by examiner

METHOXYPOLYETHYLENE GLYCOL CHELATE AND USES THEREOF

PRIORITY

This application is a continuation application of U.S. application Ser. No. 12/279,521, filed Dec. 12, 2008, now U.S. Pat. No. 8,008,347 which was a national phase application claiming priority to PCT Application No. PCT/US2007/003682, filed Feb. 14, 2007, which claims priority to U.S. Provisional Application No. 60/772,874, filed Feb. 14, 2006.

FIELD OF INVENTION

The present invention is directed generally to protecting cells, tissues, organs, and organisms including humans against the damaging effects of ionizing agents or radicals associated with radiation, chemotherapy, or with diseases or processes that result in cell damage, in which the production of free radical oxidants such as peroxides, superoxide anions, hydroxyl radicals or nitric oxides, or heavy metal cations is implicated. More particularly, the present invention is directed to novel methoxypolyethylene glycol thioester chelate esters, and to methods of using them as bioprotectants in normal or diseased humans, animals or plants, in organ transplantation and cell and tissue storage or preservation, and reduction of chemotoxicity, alone or as adjuvants with other agents or therapies. These chelate esters also will have utility in reducing intraocular pressure in glaucoma patients.

BACKGROUND OF INVENTION

In humans, exposure to ionizing radiation occurs through natural sources (such as ultraviolet or other electromagnetic radiation or cosmic radiation from the sun, stars or terrestrial radioactive sources in the earth's crust) or from various man-made sources. The primary exposure from man-made sources comes from diagnostic x-rays and radionuclide studies, dental x-rays, and therapeutic techniques (such as anticancer radiotherapy) or to a lesser extent due to fallout from atmospheric atomic weapons testing, nuclear power plants and through occupational exposure. Ionizing radiation has an adverse effect on cells and tissues, primarily through cytotoxic effects. A major way in which most forms of ionizing radiation damages biomolecules and cells is through a process called indirect action involving an interaction with water to produce toxic active oxygen species (OH., $.O^{2-}$, or $H_2O_2$). A second mechanism, called direct action, involves direct effects on DNA.

Diminution of the deleterious effects of ionizing radiation by chemoprotection would be important to a number of diverse groups, including the general population exposed to cosmic and terrestrial irradiation, to patients given diagnostic and dental x-rays, to workers exposed to irradiation, to groups exposed to radiation through accidents or acts of terrorism, to astronauts and airline personnel exposed to "extra" cosmic irradiation, and to patients given radiation to treat cancer. Approximately 60% of all cancer patients receive radiation as part of their therapy, and the harm to the normal tissues often limits the radiation dose which can be administered to the tumor. With regard to ultraviolet radiation, the increasing prevalence of melanomas, pterygium and cataracts suggest the necessity of prophylactic measures to reduce these problems.

Evidence is accumulating that the etiology of many degenerative diseases that afflict humanity includes free radical reactions. Examples of such degenerative diseases include atherosclerosis, cancer, inflammatory joint disease, arthritis, autoimmune diseases, asthma, diabetes, senile dementia, Alzheimer's disease, Parkinson's disease, multiple sclerosis, muscular dystrophy, ischemia, stroke, congestive heart failure and degenerative eye diseases. The process of biological ageing might also have a free radical element. Most free radical damage to cells involves oxygen free radicals or, more generally, activated oxygen species, which include non-radical species such as singlet oxygen and hydrogen peroxide as well as free radicals.

The eye is one organ with intense activated oxygen species activity, and it requires high levels of antioxidants to protect its unsaturated fatty acids. Glaucoma is an example of a degenerative disease of the eye that can lead to retinal cell death. Glaucoma is a widespread ocular disease of unknown etiology that can lead to eventual blindness due to gradual loss of retinal ganglionic cells (RGC). The majority of glaucoma patients have elevated intraocular pressure (IOP), and drugs capable of lowering IOP, including beta adrenergic blockers, prostanoids, cannabinoids and carbonic anhydrase inhibitors, are used clinically to reduce the impact of the disease. A significant percentage of glaucoma patients, however, do not demonstrate elevated IOP, but still show gradual reduction in ocular function due to retinal cell death. Recently, attention has focused on attempts to use neuroprotective agents to increase the survival of the retinal cells, a strategy that should be effective in all glaucoma patients.

It is now evident that ganglion cells are dependent on a variety of eurotrophins, but primarily on brain-derived neurotrophic factor (BDNF). An adult ganglion cell takes up secreted BDNF from its respective target neuron and transports it along its axon back to the cell body in the retina. Glaucoma is now thought to block this retrograde flow of BDNF by blocking axoplasmic transport at the site of the lamina cribrosa (Nickells R W., J. Glaucoma 1996; 5:345-356). It is not precisely known how long a ganglion cell can survive without its BDNF supply, but tests conducted in culture suggest that it is only a matter of days. One obvious neuroprotective strategy that has been considered for glaucoma treatment is to provide a different source of BDNF for the ganglion cells. Another damaging stimulus associated with glaucoma is the release of excitotoxins. These molecules are actually excitatory amino acids, such as glutamate, that are normally used by neurons as neurotransmitters. At high local concentrations, however, these normally benign molecules activate a highly toxic response in nearby cells (hence the derivation of the word "excitotoxin"). Like neurotrophins, excitotoxins interact with receptors on the cell surface. There are three known sub-types of glutamate receptors found on neurons, but the one that appears to play the biggest role in the excitotoxic effect is the N-methyl-D-aspartate (NMDA) receptor. Elevated levels of glutamate have been detected in the vitreous of both human glaucoma patients and monkeys with experimental glaucoma (Dreyer E B, Zurakowski D, Schumer R A, Podos S M, Lipton S A, Arch. Ophthalmol. 1996; 114:299-305).

Transition metals such as iron and copper are known to generate cytotoxic free radicals, whereas iron-regulating proteins such as transferrin, ceruloplasmin, and ferritin have been shown to act as anti-oxidants, counteracting the toxic effects of these metals. Iron and copper cations are released from tissues during ischemia and in association with a variety of disease processes. Tissues deprived of blood and oxygen undergo ischemic necrosis or infarction with possible irreversible organ damage. Even if the flow of blood and oxygen is restored to the organ or tissue (reperfusion), the organ does not immediately return to the normal pre-ischemic state. Postischemic dysfunction may be due to the generation of oxygen free radicals in the stunned organ. The re-entry of neutrophils during reperfusion can create free radical damage due to the hyper-reactivity of leukocytes. Iron and copper cations are known to catalyze hydroxy free radical formation. The chelator ethylenediaminetetraacetic acid (EDTA) is known to reduce lipid peroxidation from ionizing radiation. (Ayene-S I; Srivastava-P N Int. J. Radiat. Biol. Relat. Stud. Phys. Chem. Med. 1985 August; 48(2): 197-205). Providing anti-oxidants and reducing equivalents to ischemically stressed tissue allows recovery of the mitochondria, which is crucial in restoring normal calcium homeostasis and tissue function.

It is further known that metal cations, such as $Ca^{++}$, that are not first transition series elements perform important functions in the body, but may also be involved in a number of pathogenic processes, such as calcium overload of the heart that occurs during ischemia and reperfusion. Such metal cations can compete with cations of first transition series elements for chelation by a chelator that has a high affinity for $Ca^{++}$, and thereby interfere with the chelation of first transition series cations by the chelator. Moreover, chelation of cations such as $Ca^{++}$ can impair the normal functions of these cations in the body. Therefore, the use of chelators must be tempered with the knowledge of the role of various cations in the disease process to be treated and the selection of specific chelator affinities to remove the offending cations without creating additional ionic imbalances.

Numerous attempts have been made to reduce normal tissue damage while still delivering effective therapeutic doses of ionizing radiation to the cancerous tissue. These techniques include brachytherapy, fractionated and hyperfractionated dosing, complicated dose scheduling and delivery systems, and high voltage therapy with a linear accelerator. However, such techniques can, at best, only attempt to strike a balance between the beneficial effects of killing the cancer cells and undesirable effects of the radiation to the normal tissues. There is much room for improvement in the therapeutic ratio, which is the ratio of a measure of damage to the tumor divided by the damage to the normal tissues.

Attempts to mitigate the catalytic effectiveness of iron and copper cations by administering iron chelating siderophores such as deferoxamine to form complexes with these cations have not been unequivocally successful in inhibiting tissue damage from hydroxy free radicals in vivo. Siderophores such as deferoxamine are poor chelators for copper cations. Although present in the body in much lower concentrations than iron, copper is far more active than iron in catalyzing hydroxyl radical formation.

Polyethylene glycol (PEG) and polyethylene glycol monomethyl ether (MP) have also been found to reduce tissue injury, although the mechanism is obscure. PEG is an amphiphilic polymer $H(OCH_2CH_2)_nOH$ that consists of a mixture of homologs with a range of similar molecular weights. Thus, for example, MP 350 possesses an average molecular weight 350, and consists of a mixture of homologs with n=4 to 9, and a median n=7. The lower molecular weight polymers PEG 200-600 are absorbed through the gastrointestinal tract when ingested orally and excreted unchanged in the urine. PEG is absorbed along with water directly through the intestinal mucosal cell membrane.

PEG 200-600, being nontoxic and biologically inert, has often been used as a vehicle for administration of drugs insoluble in water. In several investigations, the PEG vehicle alone was empirically found to exhibit significant biological activity, leading to further studies of low molecular weight PEG. For example, PEG 400, when given intraperitoneally (IP) either before or shortly after x-irradiation of mice, conferred significant protection against lethality and morbidity (Shaeffer and Schellenberg, Int. J. Radiat. Oncol. Biol. Phys., 10:2329, 1984; Shaeffer, et al., Radiat. Res., 107:125, 1986). PEG 300 IP was shown to reduce the CNS sequelae of experimental concussive brain injury (Clifton, et al., J. Neurotrauma, 6:71, 1989).

PEG with a molecular weight around 400 is thus a uniquely nontoxic substance that exhibits a protective effect against injury to tissues. However, PEG with a molecular weight greater than 700 is poorly absorbed through the GI tract. The mechanism of the protective action of lower molecular weight PEG has not been established, but probably involves interaction of PEG with the surface of lipid membranes or protein components. PEG aggregates near cell membranes, reduces water polarity at membrane surfaces, and increases hydrophobic interactions (Hoekstra, et al., J. Biol. Chem., 264:6786, 1989).

It is known that certain MP chelates can be effective iron chelators. For example, it is known that MP can be linked with iminodiacetate terminus (MIDA). Other chelates modified with MP include MP 550-deferoxamine (ferrioxamine), prepared by reacting MP molecular weight 550 with carbonyldiimidazole, followed by reaction of the resulting imidazole-carbonyl ester with deferoxamine base, forming a urethane linkage. The material was produced as a chelate for gadolinium, to be used as a renal magnetic resonance contrast agent (Duewell, et al., Invest. Radiol., 26:50, 1991). Deferoxamine is known to be an effective chelator for ferric iron.

MIDA can be prepared by converting MP 350 to the chloride by reaction with thionyl chloride (Bueckmann et al., Biotechnology & Applied Biochem., 9:258-268, 1987), and to the iminodiacetate by reaction of the chloride with sodium iminodiacetate (Wuenschell et al., J. Chromatog. 543: 345-354, 1991). The methyl ester can be prepared with methanolic HCl. However, alternative MP chelates, which are more effective chelators and are non-toxic, have been sought.

U.S. Pat. No. 6,020,373 discloses that the polyethylene glycol linked to a chelate methyl ester was a very effective protectant against radiation damage and doxorubicin toxicity in animal models. The well-known radioprotectant amifostine, S-2-[3-aminopropylamino]ethylphosphorothioate (WR-2721, Ethyol), that possesses a potential thiol, has been used extensively in the clinic for protection of normal tissues in radiotherapy and chemotherapy (Wasserman, T. H., Seminars in Oncology 21(5 Supp. 11): 21-25, 1994), but its effectiveness is limited. Sulfhydryl compounds, such as cysteine and cysteamine, have been known to provide radiation protection in animals. Thiol groups scavenge radiation-produced free radicals by donating a hydrogen atom to damaged molecules. Despite extensive efforts to develop more effective protective agents, no thiol-based radioprotector has been found to be significantly better than cysteamine. Moreover, the use of thiol drugs to protect against radiation damage has been limited due to the toxicity of such compounds. Further, the use of esters of polar drugs to facilitate penetration into cells has been reported (Vos et al, Int. J. Radiat. Biol. Relat. Stud. 53:273-81, 1988).

A need clearly exists, therefore, for improved compositions and methods capable of protecting cells, tissues and organs against the damaging effects of an ionizing agent associated with radiation or chemotherapy, or with disease or other states in which the production of free radical oxidants such as peroxides, superoxide anions, hydroxyl radical or nitric oxide, or heavy metal cations is implicated.

SUMMARY OF THE INVENTION

The present invention provides compositions and methods capable of protecting cells, tissues and organs against the damaging effects of ionizing or other damaging agents associated with radiation or chemotherapy, or degenerative diseases of various organs, characterized in that they elicit the production of free radicals or oxidants such as peroxides, superoxide anions, hydroxyl radicals or nitric oxides, or heavy metal cations. More particularly, the present invention is concerned with methoxypolyethylene glycol thioester chelate methyl esters that are useful as protectors against tissue damage by penetrating the cell membrane to donate electrons to free radical oxidants and remove heavy metals that may react with peroxides to produce the reactive hydroxyl radical, or remove $Ca^{++}$ that may be released from organelles. The present invention would also be useful in reducing the elevated intraocular pressure found in various forms of glaucoma.

Accordingly, the present invention relates to a methoxypolyethylene glycol thioester compound of formula (I):

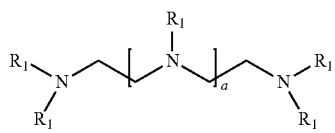

(I)

wherein one $R_1$ is formula (II)

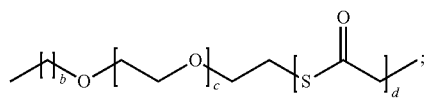

(II)

each of the remaining $R_1$ is selected from formula (II) or from the group consisting of —$CH_2COOH$, —$CH_2COO^-Na^+$, —$CH_2COO^-Ca^{++}/2$, —$CH_2COOCH_3$, —$CH_2COOC_2H_5$, and —$CH_2COOC_3H_7$; a is 0 to 6; each b is independently 0 to 18; each c is independently 3 to 10; and d is independently 1 to 3.

One embodiment of the present invention is the compound of formula (I) wherein a is 0, each b is 0, each c is independently 3 to 10, d is 1, and three $R_1$s are —$CH_2COOCH_3$. In one example the present invention is the compound of formula (I) wherein a is 0, each b is 0, each c is independently 7 or 8, d is 1, and three $R_1$s are —$CH_2COOCH_3$.

In another embodiment of the present invention is the compound of formula (I) wherein a is 1, each b is 0, each c is independently 3 to 10, d is 1, and four $R_1$s are —$CH_2COOCH_3$. In one example the present invention is the compound of formula (I) wherein a is 1, each b is 0, each c is independently 7 or 8, d is 1, and four $R_1$s are —$CH_2COOCH_3$.

More specifically, the present invention relates to compound having the following formula:

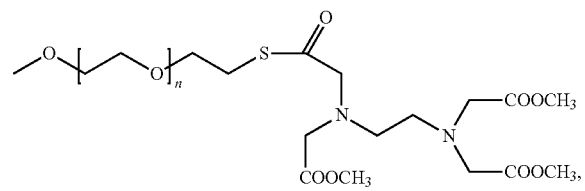

wherein n=3 to 10.

In another embodiment the present invention relates to compound having the following formula:

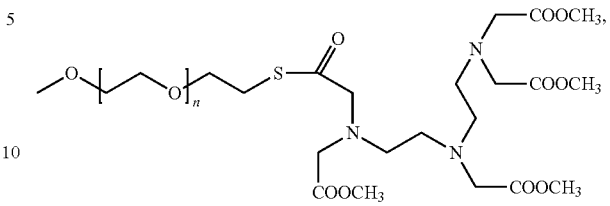

wherein n=3 to 10.

In one embodiment of the present invention, the compound of formula (I) is capable of donating electrons. In one embodiment of the present invention, the compound of formula (I) is capable of forming chelates with heavy metals or $Ca^{++}$.

The present invention is also directed to a pharmaceutical composition comprising the compound of formula (I) and at least one of a pharmaceutically acceptable carrier or a pharmaceutically acceptable adjuvant. In one embodiment, the present invention is directed to a pharmaceutical composition comprising the compound of formula (I) or a pharmaceutically acceptable salt or solvate thereof, and, optionally, at least one therapeutic agent.

The present invention is further directed to a method for preventing tissue damage resulting from exposure to radiation in a patient in need thereof comprising administering to the patient a therapeutically effective amount of the compound of formula (I).

In one embodiment, the present invention is directed to a method for preventing degenerative disease resulting from free radical oxidants in a patient in need thereof comprising administering to the patient a therapeutically effective amount of the compound of formula (I), wherein free radical oxidants comprises peroxides, superoxide anions, hydroxyl radical, and nitric oxide.

In another embodiment, the present invention is directed to a method for treating retinal cell death resulting from glaucoma in a patient in need thereof comprising administering to the patient a therapeutically effective amount of the composition comprising the compound of formula (I) and at least one of a pharmaceutically acceptable carrier or a pharmaceutically acceptable adjuvant.

In yet another embodiment, the present invention is directed to a method for donating electrons to free radical oxidants in a cell in need thereof comprising administering an effective amount of the compound of formula (I), wherein free radical oxidants comprises peroxides, superoxide anions, hydroxyl radical, and nitric oxide.

In one example, the present invention is directed to a method for preventing catalysis of free radical oxidantformation by heavy metals in a cell in need thereof comprising administering an effective amount of the compound of formula (I), wherein the free radical oxidant comprises peroxides, superoxide anions, hydroxyl radical, and nitric oxide, wherein the compound is capable of forming chelates with heavy metals.

The present invention is also directed to a kit comprising at least one compound of formula (I), or a pharmaceutically acceptable salt or solvate thereof, and instruction for use thereof.

DETAILED DESCRIPTION OF THE INVENTION

Figure 1:
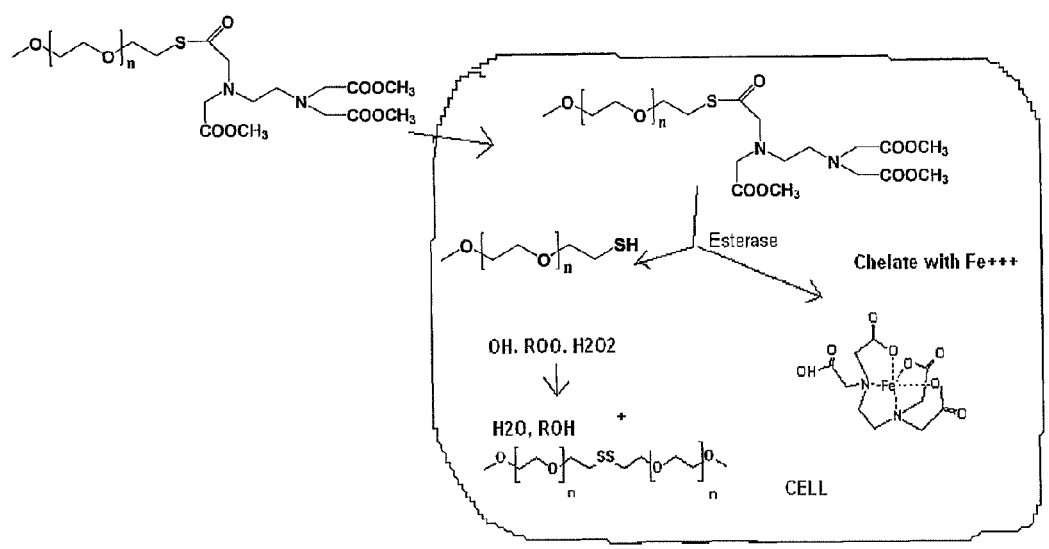
FIG. 1. illustrates an exemplary process by which the drug is hydrolyzed to MPthiol which donates electrons to free radical oxidants while the chelate removes heavy metals produced by cell damage.

The present invention provides novel compounds for use in protecting cells, tissues, organs, and organisms against the damaging effects of ionizing agents associated with radiation or chemotherapy, or degenerative diseases of various organs, that elicits the production of free radicals, superoxide anions, or heavy metal cations. In one aspect, the present invention is directed to a combination of a potential thiol with a potential chelate, together with the amphiphilic polyethylene glycol tail that facilitates transport into cells, to allow for a dual protective mechanism against free radical damage to cells.

In one aspect, the present invention is directed to novel amphiphilic cell-penetrating methoxypolyethylene glycols (MP) with an average weight of 200 to 600, more preferably 300 to 450, and most preferably 350 (MP 350), which are modified by chemically attaching chelating groups onto the non-methyl end of the polymer by a thioester linkage.

Exemplary chelating groups that can be used to modify the methoxypolyethylene glycols of the invention include ethylenediaminetetraacetic acid (EDTA), diethylenetriaminepentaacetic acid (DTPA) and similar chelating groups formed, for example, by reaction of bromoacetic acid or derivatives to triethylenetetramine and other higher homologs containing ethylenamine linkages, or other chelating groups such as cyclohexanediaminetetraacetic acid and ethylene glycol aminoethyl ether tetraacetic acid (EGTA).

The compounds of the present invention generally have the following formula:

$$\text{(I)}$$

wherein one $R_1$ is formula (II)

$$\text{(II)}$$

each of the remaining $R_1$ is selected from formula (II) or from the group consisting of —$CH_2COOH$, —$CH_2COO^-Na^+$ or other monovalent ion, —$CH_2COO^-Ca^{++}/2$ or other divalent or multivalent ion, —$CH_2COOCH_3$, —$CH_2COOC_2H_5$, and —$CH_2COOC_3H_7$;

a is 0 to 6; each b is independently 0 to 18; each c is independently 3 to 10; and d is independently 1 to 3.

One embodiment of the present invention is the compound of formula (I) wherein a is 0, each b is 0, each c is independently 3 to 10, preferably 7, d is 1, one $R_1$ is formula (II), and three $R_1$s are —$CH_2COOCH_3$.

Another embodiment of the present invention is the compound of formula (I) wherein a is 1, each b is 0, each c is independently 3 to 10, preferably 7, d is 1, one $R_1$ is formula (II), and remaining $R_1$s are —$CH_2COOCH_3$.

In one example, compound of the present invention is methoxypolyethlene glycol thioester of ethylenediaminetetraacetic acid methyl triester (MPSEDE) having the following formula:

wherein n=3 to 10, preferably 7.

In another example, compound of the present invention is methoxypolyethlene glycol thioester of diethylenetriaminepentaacetic acid methyl tetraester having the following formula wherein n=3 to 10, preferably 7.

The present invention further provides a process for the preparation of a compound of formula (I) as defined above which comprises the steps of first converting MP to the chloride by reaction with thionyl chloride (Bueckmann et al., Biotechnology & Applied Biochem., 9:258-268, 1987), and then to a thiol (MPthiol) by reaction of the chloride with thiourea (Urquhart et al Organic Syntheses Coll. Vol 3; Horning, E. C.; Ed.; Wiley, N.Y., 1955; pp 363-365). MPthiol was coupled to the chelators as a thioester using carbonyldiimidazole as coupling agent with dimethylformamide solvent (Gais, Angew. Chem. Int. Ed. 16:244-246, 1977), followed by methyl esterification of the other carboxyl groups with methanol and carbonyldiimidazole. Methoxypolyethlene glycol thioester of ethylenediamine tetraacetic acid (MPSEDE) and methoxypolyethlene glycol thioester of diethylenetriamine pentaacetic acid (MPSDTE) can be prepared in the same manner by coupling the MPthiol with EDTA and DTPA respectively.

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or paratoluenesulphonate.

Compounds of formula (I) may exist in stereoisomeric forms. It will be understood that the invention encompasses the use of all geometric and optical isomers of the compounds of formula (I) and mixtures thereof including racemates. The use of tautomers and mixtures thereof also forms a contemplated aspect of the present invention.

Compounds of formula (I) may include other chelators or reducing groups, such as BAPTA, TPEN (tetrakis-(2-pyridyl-methyl)ethylenediamine), calcein as chelators and NADH and NAD(P)H as reducing groups.

A particularly important feature of the compounds of the invention is their ability to penetrate the cell membrane. In one embodiment, the present invention is directed to novel amphiphilic cell-penetrating methoxypolyethylene glycols (MP) with an average weight of 200 to 600, more preferably 300 to 450, and most preferably 350 (MP 350), which are modified by chemically attaching chelating groups onto the non-methyl end of the polymer by linkages that include functional groups such as selenium, sulfoxide, reductones containing the enediol group (such as ascorbic acid and dihydroxymaleic acid), hydroquinines, dihydropyridines, tetrasubstituted hydroquinone ethers including the tocopherol ring system, dithiols including dihydrolipoic acid, indoles, and conjugated polyenes including carotenoids that result in radical-reducing agents. Other chelates may include chelates with carbamate groups in place of carboxyl including deferoxamine, and heterocyclic amines including ortho-phenanthroline, 1,1-dipyridyl, and 8-hydroxyquinoline. In one example, compounds of the present invention includes MP thioesters of cyclohexanediaminetetraacetic acid and ethylene glycol aminoethyl ether tetraacetic acid (EGTA), which are synthesized by substituting EDTA with cyclohexanediaminetetraacetic acid or EGTA during the step involving coupling MPthiol to a chelate with carbonyldiimidazole.

While not intending to be bound by any particular theory of action, this ability to penetrate the cell membrane is believed to be the result of non-polarity conferred by the amphiphilic MP and the nonpolar ester groups, possibly through membrane channels used for nonpolar metabolites, followed by rapid activation by intracellular esterases to the thiol and the active chelate. The thiol is thought effective in donating electrons to free radical oxidants such as peroxides, superoxide, hydroxyl radical, or nitric oxide, with formation of the disulfide, while the chelate is believed to remove heavy metals, such as $Fe^{-+}$, $Fe^{+++}$ or $Cu^{++}$, produced by cell damage, and that may react with peroxides to produce the reactive hydroxyl radical, or remove $Ca^{++}$ that may be released from organelles. The compounds of the invention thus have the capability of protecting cells by two different mechanisms. This process is illustrated in FIG. 1.

In a further aspect, the present invention provides the use of a compound of formula (I), or a pharmaceutically acceptable salt or solvate thereof, in the manufacture of a medicament for use in therapy. It is understood that the medicament may include other components or pharmaceutically acceptable adjuvant with different or similar mechanisms of action permitting a broader scope of prophylaxis or therapeutic effect than the MP ester or salt alone. The term "adjuvant" is intended to be construed as an ingredient that modifies the action of the principal ingredient or an ingredient that enhances the effectiveness of medical treatment or an ingredient that enhances the immune response to an antigen In the context of the present specification, the term "therapy" also includes "prophylaxis" unless there are specific indications to the contrary. The terms "therapeutic" and "therapeutically" are intended to be construed accordingly.

The invention provides a safe and effective method of treating Alzheimer's in a patient suffering from, or at risk of, this debilitating neurodegenerative disease, which comprises administering to a patient in need thereof a therapeutically effective amount of a compound of formula (I), or a pharmaceutically acceptable salt or solvate thereof.

The invention also provides a safe and effective method of treating Parkinson's disease in a patient suffering from, or at risk of, said disease, which comprises administering to the patient a therapeutically effective amount of a compound of formula (I), or a pharmaceutically acceptable salt or solvate thereof.

The invention also provides a safe and effective method of treating multiple sclerosis (MS) in a patient suffering from, or at risk of, said disease, which comprises administering to the patient a therapeutically effective amount of a compound of formula (I), or a pharmaceutically acceptable salt or solvate thereof.

The invention still further provides a safe and effective method of treating muscular dystrophy (MD) in a patient suffering from, or at risk of, said disease, which comprises administering to the patient a therapeutically effective amount of a compound of formula (I), or a pharmaceutically acceptable salt or solvate thereof.

The invention provides a safe and effective method of treating radiation damage and the prevention of radiation-related cancers in a patient in need thereof by administering to the patient a therapeutically effective amount of a compound of formula (I), a pharmaceutically acceptable salt or solvate thereof, or a pharmaceutically acceptable adjuvant thereof. The source of radiation may be electromagnetic, including visible or ultraviolet light, or nuclear, including alpha, beta, gamma, or cosmic radiation. The types of damage may include, but is not limited to, various forms of dermatological damage, such as sunburn, age spots and melanomas, as well as internal cell loss, cyst formation, neuropathies and various types of benign and malignant tumors.

The invention provides a safe and effective method of treating toxicity to normal tissues from chemotherapy in a patient in need thereof, or inadvertent or intentional administration of chemical agents having a free radical and/or heavy metal toxicological component, by administering to the patient a therapeutically effective amount of a compound of formula (I), a pharmaceutically acceptable salt or solvate thereof, or a pharmaceutically acceptable adjuvant thereof and one or more chemical agents having a free radical and/or heavy metal toxicological components. The compound of formula (I) may be administered before, during or after administration of the chemical agents having a free radical and/or heavy metal toxicological components. The invention is useful for reducing the toxicity of chemical agents having a free radical and/or heavy metal toxicological components including fluoropyrimidines, pyrimidine nucleosides, purines, platinum analogues, antroacyclines, podophyllotoxins, camptothecins, hormones and hormone analogues, enzymes, proteins and antibodies, vinca alkaloids, taxanes, and the like. While the present method for reducing toxicity is applicable for any chemotherapeutic agent some exemplary ones are irinotecan, FU, taxol, cisplatin adriamycin, oxaliplatin, cyclophasphamide, EGF and VGF inhibitors, acemannan, acetaminophen, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), SU 6668 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The invention provides a safe and effective method of treating ischemia in a patient suffering from, or at risk of, said disease, which comprises administering to the patient a therapeutically effective amount of a compound of formula (I), or a pharmaceutically acceptable salt or solvate thereof.

The invention also provides a safe and effective method of treating stroke in a patient suffering from, or at risk of, said disease, which comprises administering to the patient a therapeutically effective amount of a compound of formula (I), or a pharmaceutically acceptable salt or solvate thereof.

The invention also provides a safe and effective method of treating congestive heart failure in a patient suffering from, or at risk of, said disease, which comprises administering to the patient a therapeutically effective amount of a compound of formula (I), or a pharmaceutically acceptable salt or solvate thereof.

The invention still further provides a safe and effective method of treating ocular diseases in a patient suffering from, or at risk of, said diseases, which comprises administering to the patient in need thereof a therapeutically effective amount of a compound of formula (I), or a pharmaceutically acceptable salt or solvate thereof. Other diseases can include any presently known to medical science, including but not limited to glaucoma, macular degeneration, cataracts, melanomas, pterygium, and the like.

The invention still further provides a safe and effective method of treating neurodegenerative, rheumatological, arthritic or autoimmune diseases in a patient suffering from, or at risk of, said diseases, which comprises administering to the patient a therapeutically effective amount of a compound of formula (I), or a pharmaceutically acceptable salt or solvate thereof. Other diseases can include any presently known to medical science, including but not limited to various forms of arthritis, Crohn's disease, fibromuscular dysplasia, and the like.

The invention provides a safe and effective method for cell, tissue or organ preservation in a patient in need thereof by administering to the patient a therapeutically effective amount of a compound of formula (I), or a pharmaceutically acceptable salt or solvate thereof.

The invention provides a safe and effective method for treatment or prevention of iron or other heavy metal or transition element toxicity in a patient in need thereof by administering to the patient a therapeutically effective amount of a compound of formula (I), or a pharmaceutically acceptable salt or solvate thereof.

The invention provides a safe and effective method for protection of isolated organs, tissue, cells including blood cells, sperm, plant cells, extracts, membranes, liposomes, proteins, carbohydrates, lipids, DNA or other natural or synthetic biological materials by including in the medium a therapeutically effective amount of a compound of formula (I), or a pharmaceutically acceptable salt or solvate thereof.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt, ester, or solvate thereof, as herein defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt, ester, or solvate thereof, as herein described, with a pharmaceutically acceptable adjuvant, diluent or carrier. The carrier(s) must be "acceptable" in the sense of being compatible with the other ingredients of the formulation and not deleterious to the recipient thereof.

The pharmaceutical compositions may be administered topically (e.g., to the lung and/or airways or to the skin or other epithelial surface) in the form of solutions, suspensions, native or heptafluoroalkane aerosols and dry powder formulations; or systemically, e.g., by oral administration in the form of tablets, capsules, syrups, powders or granules, or by parenteral administration in the form of solutions or suspensions, or by subcutaneous administration or by vaginal or rectal administration in the form of suppositories, or transdermally.

The compounds and compositions of the present invention can be administered by any available and effective delivery system including, but not limited to, orally, bucally, within the ear or nasal passages, parenterally, by inhalation spray, by topical application, by injection, transdermally, vaginally or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, pastes, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400 which may function as solvent or absorption modifier. They can be mixed to form ointments with, for example, benzyl alcohol 2% (wt/wt) as preservative, white petrolatum, emulsifying wax, and Tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous cross linking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the present invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention can be prepared by mixing the compounds or compositions with a suitable nonirritating excipient such as cocoa butter and polyethylene glycols which are solid at room temperature but liquid at body temperature, such that they will melt and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of the invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylase, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances that increase the viscosity of the suspension and include, for example, sodium carboxymethyl cellulose, sorbitol and/or dextran. Optionally, the suspension may also contain stabilizers.

Solvents useful in the practice of this invention include pharmaceutically acceptable, water-miscible, non-aqueous solvents. In the context of this invention, these solvents should be taken to include solvents that are generally acceptable for pharmaceutical use, substantially water-miscible, and substantially non-aqueous. Preferably, these solvents are also non-phthalate plasticizer leaching solvents, so that, when used in medical equipment, they substantially do not leach phthalate plasticizers that may be present in the medical equipment. More preferably, the pharmaceutically-acceptable, water-miscible, non-aqueous solvents usable in the practice of this invention include, but are not limited to, N-methylpyrrolidone (NMP); propylene glycol; ethyl acetate; dimethyl sulfoxide; dimethyl acetamide; benzyl alcohol; 2-pyrrolidone; benzyl benzoate; $C_{2-6}$ alkanols; 2-ethoxyethanol; alkyl esters such as 2-ethoxyethyl acetate, methyl acetate, ethyl acetate, ethylene glycol diethyl ether, or ethylene glycol dimethyl ether; (S)-(−)-ethyl lactate; acetone; glycerol; alkyl ketones such as methyl ethyl ketone or dimethyl sulfone; tetrahydrofuran; cyclic alkyl amides such as caprolactam; decylmethylsulfoxide; oleic acid; aromatic amines such as N,N-diethyl-m-toluamide; or 1-dodecylazacycloheptan-2-one.

The compositions of this invention can further include solubilizers. Solubilization is a phenomenon that enables the formation of a solution. It is related to the presence of amphiphiles, that is, those molecules that have the dual properties of being both polar and non-polar in the solution that have the ability to increase the solubility of materials that are normally insoluble or only slightly soluble, in the dispersion medium. Solubilizers often have surfactant properties. Their function may be to enhance the solubility of a solute in a solution, rather than acting as a solvent, although in exceptional circumstances, a single compound may have both solubilizing and solvent characteristics. Solubilizers useful in the practice of this invention include, but are not limited to, triacetin, polyethylene glycols (such as, for example, PEG 300, PEG 400, or their blend with 3350, and the like), polysorbates (such as, for example, Polysorbate 20, Polysorbate 40, Polysorbate 60, Polysorbate 65, Polysorbate 80, and the like), poloxamers (such as, for example, Poloxamer 124, Poloxamer 188, Poloxamer 237, Poloxamer 338, Poloxamer 407, and the like), polyoxyethylene ethers (such as, for example, Polyoxyl 2 cetyl ether, Polyoxyl 10 cetyl ether, and Polyoxyl 20 cetyl ether, Polyoxyl 4 lauryl ether, Polyoxyl 23 lauryl ether, Polyoxyl 2 oleyl ether, Polyoxyl 10 oleyl ether, Polyoxyl 20 oleyl ether, Polyoxyl 2 stearyl ether, Polyoxyl 10 stearyl ether, Polyoxyl 20 stearyl ether, Polyoxyl 100 stearyl ether, and the like), polyoxylstearates (such as, for example, Polyoxyl 30 stearate, Polyoxyl 40 stearate, Polyoxyl 50 stearate, Polyoxyl 100 stearate, and the like), polyethoxylated stearates (such as, for example, polyethoxylated 12-hydroxy stearate, and the like), and Tributyrin.

Other materials that may be added to the compositions of the present invention include cyclodextrins, and cyclodextrin analogs and derivatives, and other soluble excipients that could enhance the stability of the inventive composition, maintain the product in solution, or prevent side effects associated with the administration of the inventive composition. Cyclodextrins may be available as ENCAPSIN® from Janssen Pharmaceuticals.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the present invention, including, for example, encapsulation in liposomes, microbubbles, emulsions, microparticles, microcapsules, nanoparticles, and the like. The required dosage can be administered as a single unit or in a sustained release form.

The bioavailabilty of the compositions can be enhanced by micronization of the formulations using conventional techniques such as grinding, milling, spray drying and the like in the presence of suitable excipients or agents such as phospholipids or surfactants.

Sustained release dosage forms of the invention may comprise microparticles and/or nanoparticles having a therapeutic agent dispersed therein or may comprise the therapeutic agent in pure, preferably crystalline, solid form. For sustained release administration, microparticle dosage forms comprising pure, preferably crystalline, therapeutic agents are preferred. The therapeutic dosage forms of this aspect of the present invention may be of any configuration suitable for sustained release. Preferred sustained release therapeutic dosage forms exhibit one or more of the following characteristics: microparticles (e.g., from about 0.5 micrometers to about 100 micrometers in diameter, preferably about 0.5 to about 2 micrometers; or from about 0.01 micrometers to about 200 micrometers in diameter, preferably from about 0.5 to about 50 micrometers, and more preferably from about 2 to about 15 micrometers) or nanoparticles (e.g., from about 1.0 nanometer to about 1000 nanometers in diameter, preferably about 50 to about 250 nanometers; or from about 0.01 nanometer to about 1000 nanometers in diameter, preferably from about 50 to about 200 nanometers), free flowing powder structure; biodegradable structure designed to biodegrade over a period of time between from about 0.5 to about 180 days, preferably from about 1 to 3 to about 150 days, more preferably from about 3 to about 180 days, and most preferably from about 10 to about 21 days; or non-biodegradable structure to allow the therapeutic agent diffusion to occur over a time period of between from about 0.5 to about 180 days, more preferably from about 30 to about 120 days; or from about 3 to about 180 days, more preferably from about 10 to about 21 days; biocompatible with target tissue and the local physiological environment into which the dosage form to be administered, including yielding biocompatible biodegradation products; facilitate a stable and reproducible dispersion of therapeutic agent therein, preferably to form a therapeutic agent-polymer matrix, with active therapeutic agent release occurring by one or both of the following routes: (1) diffusion of the therapeutic agent through the dosage form (when the therapeutic agent is soluble in the shaped polymer or polymer mixture defining the dimensions of the dosage form); or (2) release of the therapeutic agent as the dosage form biodegrades; and/or for targeted dosage forms, capability to have, preferably, from about 1 to about 10,000 binding protein/peptide to dosage form bonds and more preferably, a maximum of about 1 binding peptide to dosage form bond per 150 square angstroms of particle surface area. The total number of binding protein/peptide to dosage form bonds depends upon the particle size used. The binding proteins or peptides are capable of coupling to the particles of the therapeutic dosage form through covalent ligand sandwich or non-covalent modalities as set forth herein.

Nanoparticle sustained release therapeutic dosage forms are preferably biodegradable and, optionally, bind to the vascular smooth muscle cells and enter those cells, primarily by endocytosis. The biodegradation of the nanoparticles occurs over time (e.g., 30 to 120 days; or 10 to 21 days) in prelysosomic vesicles and lysosomes. Preferred larger microparticle therapeutic dosage forms of the present invention release the therapeutic agents for subsequent target cell uptake with only a few of the smaller microparticles entering the cell by phagocytosis. A practitioner in the art will appreciate that the precise mechanism by which a target cell assimilates and metabolizes a dosage form of the present invention depends on the morphology, physiology and metabolic processes of those cells. The size of the particle sustained release therapeutic dosage forms is also important with respect to the mode of cellular assimilation. For example, the smaller nanoparticles can flow with the interstitial fluid between cells and penetrate the infused tissue. The larger microparticles tend to be more easily trapped interstitially in the infused primary tissue, and thus are useful to deliver anti-proliferative therapeutic agents.

Preferred sustained release dosage forms of the present invention comprise biodegradable microparticles or nanoparticles. More preferably, biodegradable microparticles or nanoparticles are formed of a polymer containing matrix that biodegrades by random, nonenzymatic, hydrolytic scissioning to release therapeutic agent, thereby forming pores within the particulate structure.

The compounds and compositions of the present invention can be formulated as pharmaceutically acceptable esters or salts. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitrous (nitrite salt), nitric (nitrate salt), carbonic, sulfuric, phosphoric acid, and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, parahydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The present invention may be administered in the following doses: internal 1 pg/kg to 10 g/kg; topical 0.00001% to 100%, formulated as preparations for immediate or sustained release. The dosing regimens of the present invention include discrete doses of between 1 and 8 administrations per day, acute single dose, and chronic multiple dose, as drip (constant IV or other infusion), or as bolus. The invention may be formulated with solvent and other agents or compounds.

The present invention also provides pharmaceutical kits comprising one or more containers filled with one or more of the ingredients of the pharmaceutical compounds and/or compositions of the present invention, including, one or more therapeutic agents described herein. Such kits can also include, for example, other compounds and/or compositions (e.g., therapeutic agents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

EXAMPLES

A more complete understanding of the present invention can be obtained by referring to the following illustrative examples of the practice of the invention, which examples are not intended, however, to limit the invention. In the following illustrative examples, fast atom bombardment mass spectra (FAB MS) were acquired on a MS50-TA mass spectrometer, at Washington University, St. Louis, using a matrix of nitrobenzyl alcohol and lithium ion and xenon gas FAB beam to ionize the samples. The instrument is a three sector, EBE design with maximum resolving power of 50,000. Mass range at full accelerating potential (8 kV) is about 800 Daltons. Low resolution FAB spectra are run at a nominal resolution of 1000 and high resolution spectra are run at 10,000 resolution. Accurate mass measurement is accomplished by peak matching technique using an alkali metal salt ion as the reference mass.

All solvents and commercial reagents were laboratory grade and used as received. The MPthiol-linked chelate esters were tested biologically for maximum tolerated dose (MTD)

or LD 50, radioprotection, and as scavenger compounds for glaucoma treatment. The MPthiol was tested as a radioprotectant. Attachment of MPthiol to EDTA or DTPA results in derivatives that are of comparable toxicity to the parent compounds. The compounds were prepared in several steps from methoxypolyethene glycol (MP) and the chelate EDTA or diethylenetriaminepentaacetic acid (DTP).

Example 1

Methyl Ester of Methoxypolyethlene Glycol Thiol with EDTA (MPSEDE)

Figure 2:
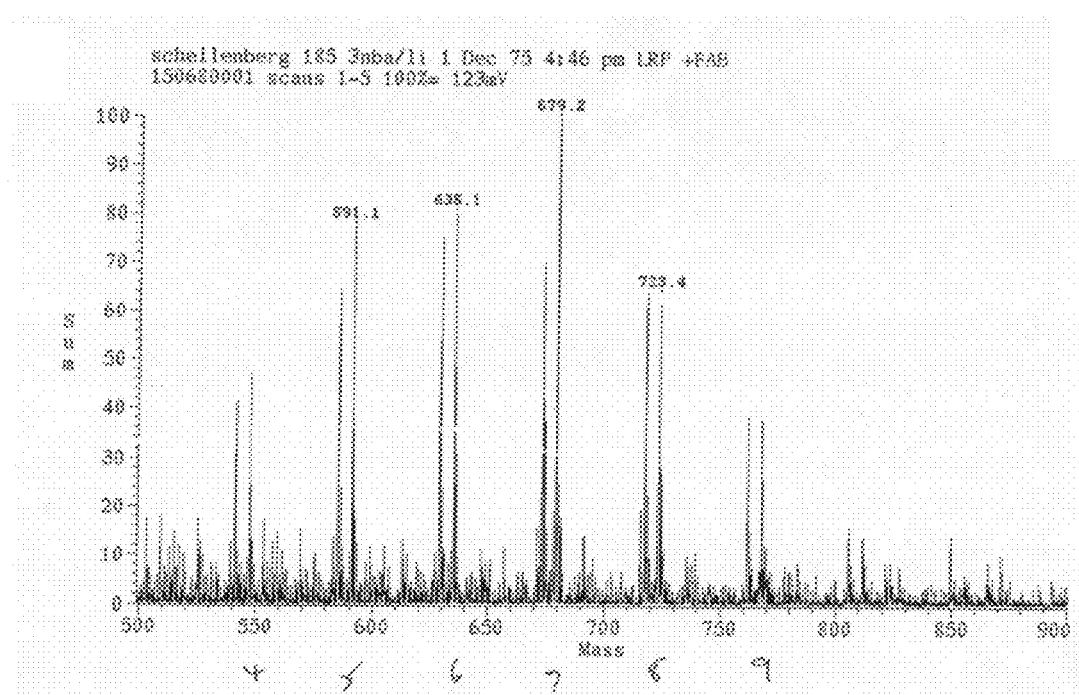
FIG. 2 illustrates a representative mass spectrum of methoxypolyethlene glycol thiol coupled with EDTA methyl triester (MPSEDE).

MP was converted to the chloride by reaction with thionyl chloride (Bueckmann, et al., Biotech. Appl. Biochem., 9: 258-268, 1987) thence to the thiol by reaction with thiourea (Urquhart et al Organic Syntheses Coll. Vol 3; Horning, E. C.; Ed.; Wiley, N.Y., 1955; pp 363-365) followed by treatment with base, acid, and purified by silica gel chromatography. The thiol was coupled to the EDTA as a thioester using carbonyldiimidazole as coupling agent with dimethylformamide solvent (Gais, Angew. Chem. Int. Ed. 16:244-246, 1977), followed by methyl esterification of the other carboxyl groups with methanol and carbonyldiimidazole. The products were purified by silica gel chromatography with elution by a gradient of ethyl acetate and heptane, and characterized by saponification and determination of chelate by copper chloride titration with pyridylazonaphthol indicator (Blijenberg et al., Clin. Chim Acta 26:577-579, 1969), determination of thiol by spectrophotometry with Ellman's reagent (Riddles et al Meth. Enzymol. 1983, 91, 49-60), and confirmation of the molecular structure by FAB mass spectrometry. All of the analyses were consistent with the structures shown. A representative mass spectrum of MPSEDE is shown in FIG. 2. The product consisted of the chelate coupled to MPthiol with number of ethoxy units from 4 to 9, with M+H and M+Li peaks shown.

Example 2

Methyl Ester of Methoxypolyethlene Glycol Thiol with DTPA (MPSDTE)

MP was converted to MPthiol using the same process described in Example 1. The thiol was coupled to the DTPA as a thioester using carbonyldiimidazole as coupling agent with dimethylformamide solvent (Gais, Angew. Chem. Int. Ed. 16:244-246, 1977), followed by methyl esterification of the other carboxyl groups with methanol and carbonyldiimidazole. The products were purified by silica gel chromatography with elution by a gradient of ethyl acetate and heptane, and characterized by saponification and determination of chelate by copper chloride titration with pyridylazonaphthol indicator (Blijenberg et al, Clin. Chim Acta 26:577-579, 1969), determination of thiol by spectrophotometry with Ellman's reagent (Riddles et al Meth. Enzymol. 1983, 91, 49-60), and confirmation of the molecular structure by FAB mass spectrometry. All of the analyses were consistent with the structures shown.

Toxicity Studies

For all biological studies, the substances were dissolved in water and adjusted to pH 7. Preliminary determination of the approximate toxicity level of the substances was by intraperitoneal (IP) injection of increasing doses into individual Swiss-Webster female mice until toxicity was evident. The maximum tolerated dose (MTD) was 2 mmole per kilogram without evident toxic symptoms such as coma, convulsions, or death.

Radioprotection Studies

The effect of MPthiol derivatives on radiation lethality was tested. Groups of 12 or more female Swiss-Webster mice were given IP solutions of the derivatives at a dose of approximately one-half of the maximum tolerated dose. Ten minutes later, pentobarbital (PB) 0.262 mmole/kg was given IP, and twenty minutes after the first injection, the head and neck were irradiated at various doses indicated at time 20 to 50 minutes. The irradiation was performed using the Philips RT-250 unit operated under the following conditions: 200 kVp, 20 mA, 0.2 mm Cu added filtration, HVL 0.57 mm Cu, dose rate of 1.834 Gy/min. Mice were irradiated in groups of 6 or 12, and their heads were arranged within a 20×24 cm aperture cone at a 50 cm target-to-skin distance such that all their heads were within a 95% isodose. The output of the X-ray unit was calibrated using a Capintec PT-06C Farmer chamber. Controls received only PB and 0.4 ml normal saline in place of the drug.

Figure 3:
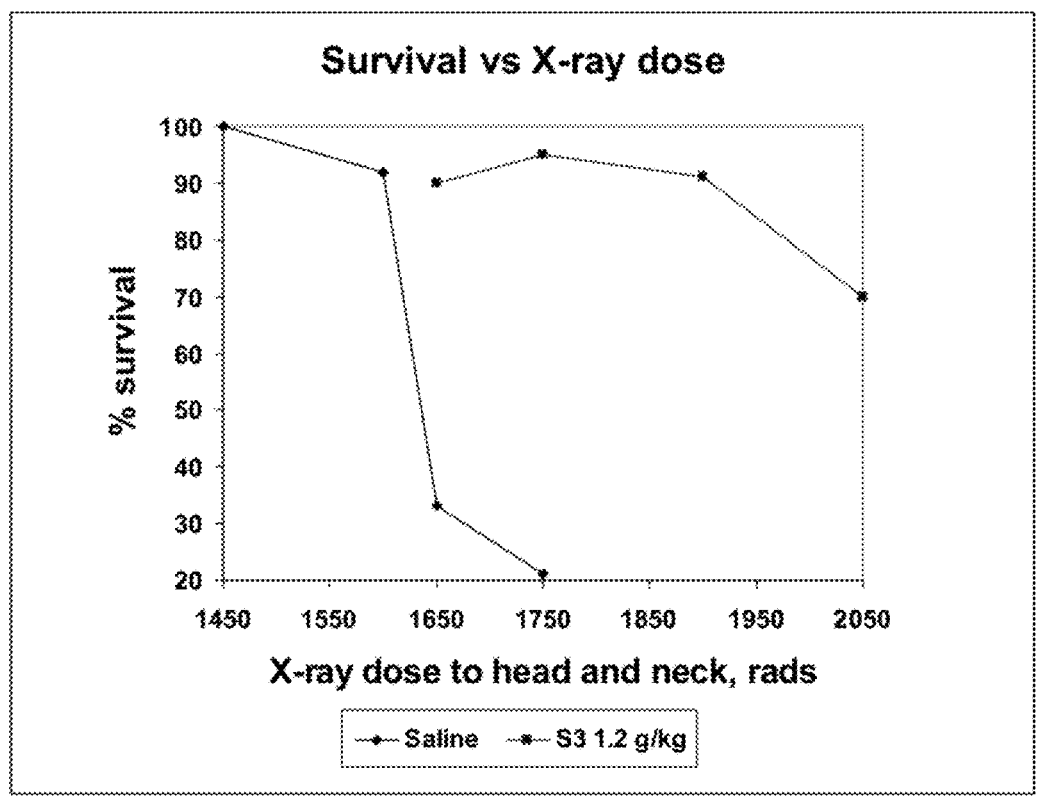
FIG. 3 illustrates the effectiveness of MPthiol compounds as radioprotectant.

The mice were examined for general condition and survival, and the mortality noted for each group. Under these conditions the mice died from radiation between 10 and 13 days following exposure. FIG. 3 illustrates the percent survival of these mice after the administration of MPthiol or saline followed by irradiation to head and neck at various doses. MPthiol was found to be an effective radioprotectant, with a dose modification factor comparable with known radioprotectors such as amifostine (Ethyol).

Effect on Surgically Induced Glaucoma

MPSEDE was tested in rats for protection against glaucoma and retinal ganglion cell loss.

Rat Ocular Hypertensive Model:

Ocular hypertension was induced in 9 male SpragueDawley rats, weighing between 400 to 500 grams. Under general anesthesia with acepromazine maleate (12 mg/Kg) and ketamine (80 mg/Kg), IP, and topical proparacaine (0.5%), dissection of the conjunctiva was made with fine cuts. To reduce the stimulus for revascularization or neovascularization, dissection of the right eye was limited to the area immediately surrounding the vortex veins. Three of four vortex veins were exposed and ligated using 9.0 nylon sutures. Criterion for inclusion into the study was an intraocular pressure (IOP) increase of 5 mm Hg or more when compared to cryosurgical baseline IOP. Within 6 weeks, the IOP of all the operated eyes increased at least 5 mm Hg compared to baseline. National Institutes of Health Guidelines and Association for Research in Vision and Ophthalmology statement for the Use and Care of Animals were followed in this study.

Intraocular Pressure (IOP) Measurements:

Prior to initiation of treatment, baseline IOP was obtained in glaucoma rat models. IOP was measured via a specially modified Goldmann applanation tonometer (HAAG-STREIT, Bern, Switzerland) under sedation. Measurements are averages of two consecutive readings and were made at the same time of day and by the same observers.

Measurement of Ocular Damage:

Slit lamp (HAAG-STREIT, Bern, Switzerland) examination was performed to determine any possible ocular damage and changes in the anterior chamber. Examinations were documented by a semi-quantitative scale which was modified to document signs of inflammation, conjunctival chemosis/ swelling, conjunctival discharge, aqueous flare, fibrin, light reflex, iris, corneal opacity, vascularization and staining (Samudre, S S, Lattanzio, F A Jr., Williams, P B, and Sheppard, J D, Jr., Comparison of topical steroids for acute anterior uveitis, J. Ocul. Phamacol. Ther. (2004) 20:533-47). Prior to examination, rats were sedated with acepromazine maleate (6 mg/Kg), and ketamine (40 mg/Kg), plus topical administration of 0.5% proparacaine. Throughout the course of the study, this examination was performed by the same group of masked, knowledgeable observers.

In Vivo Analysis by Confocal Microscopy:

This technique permits repeated in vivo visualization of cornea and anterior segment for the presence, location and number of inflammatory cells, as well as fibrin, hyper-refractive bodies and changes in epithelial, stromal and endothelial cell morphology. Rats were examined under acepromazine (12 mg/Kg) and ketamine (80 mg/Kg) anesthesia, plus topical administration of 0.5% proparacaine using an Advanced Scanning Limited confocal microscope (ASL 1000, Advanced Scanning Limited, New Orleans, La.), documented using a CCD camera (Kappa Optoelectronics Inc., Monrovia, Calif.) and recorded with SVO-9500MD VCR (Sony Corporation, Tokyo, Japan). Data was analyzed using Metamorph™ imaging system (Universal Imaging, Downingtown, Pa.).

NMDA Retinal Damage Model:

Changes in electroretinogram (ERG) A and B waves have been used as indicators of RGC damage. To examine RGC neuroprotection, 2 ul intravitreal injections of 10 mM NMDA, sufficient to change ERG A and B-waves within 2 weeks, were challenged with co-administered intravitreal (2 mM) or topical 100 mM MPDTE, MPSEDE and amifostine in normal rats unilaterally. For topical administration, rats were pretreated for 5 days prior and 3 days post-NMDA administration with the agents at a frequency of 3 times per day with 20 µl agent. Scotopic ERG changes were measured in normal rats. Rats were dark adapted for at least 4 hrs. Eyes were dilated with atropine after which proparacaine and methylcellulose gel were applied topically. Custom made AgCl electrodes (64-1317, Warner Instruments, Hamden, Conn.) were placed on the apex of the cornea. Stimuli consisted of 10-microsec flashes of unattenuated white light generated by Ganzfield bowl photo stimulator (Grass Instruments, PS22, Quincy, Mass.). Data from each eye was recorded separately with a driver amplifier (Grass Instruments, Model 7DAF Polygraph, Quincy, Mass.). Data was acquired digitally via DASYLab (Bedford, N.H.). The contralateral normal eye served as an age matched negative control, e.g. response in a normal, undamaged eye. Differences in amplitude of the A-wave and B-waves between the treated eye and the contralateral eye and between treatment groups were calculated.

Topical Application of MP Compounds for IOP Measurements on Rat Surgical Glaucoma Model:

Rats were treated topically with 20 µl of MP compounds (0.3-100 mM; n=3-6) on the operated eyes. The MP compounds were compared to 10 or 87 mM topical amifostine, a free radical scavenger. MP esterified chelators were diethylenetriaminepentaacetic acid (MPDTE) and MPSEDE.

Chronic Test of MPDTE Ocular Toxicity:

Two groups of normal rats were tested with 20 µl topical doses in one eye of 10 mM MPDTE (n=3) or 87 mM MPDTE (n=3) with 3 daily doses for 1 month. IOP, slit lamp and confocal examinations were done prior to drug administration a slit lamp examination at 15 days and IOP, slit lamp and confocal examinations 30 days later.

Pharmacokinetic Experiments:

To determine topical absorption and systemic distribution of MP compounds, $^{14}$C-labeled MPDTE was administered to normal rats in a 20 µl drop of 30 mM MPDTE. The $^{14}$C label was attached to the MP backbone to reduce the chance of spurious exchange. After 15-120 minutes with 2-6 animals per time point, the animals were euthanized and blood, urine and tissue samples were obtained. The eyes were enucleated and rinsed 5 times with 0.9% saline to remove unabsorbed drug. Samples were solubilized and counted in a liquid scintillation counter to determine the presence of the radiolabeled MP.

Data Analysis:

One Way Analysis of Variance used to analyze IOP, blood pressure and heart rate data. The paired t-test was used for pair wise comparisons. Non-parametric data were analyzed by the signed ranks test. A difference of $P<0.05$ was considered statistically significant. All values reported as mean±SEM unless otherwise noted.

Doxorubicin Chemotoxicity Studies on H9C2 Cells

H9C2 cells, which are used as models for rat striated muscle, were cultured using techniques described previously (Lattanzio, F A Jr., Tiangco, D., Osgood, C., Beebe, S., Kerry, J. and Hargrave B Y. Cocaine increases intracellular calcium and reactive oxygen species, depolarizes mitochondria, and activates genes associated with heart failure and remodeling. Cardiovascular Toxicology (20050 5: 377-389). Fluorescent calcium indicator and ROS indicator were used to determine if the reported increase in intracellular calcium and ROS activity occurred and whether these changes were reduced in the presence of 2 mM MPSEDE or MPDTE. Cells were measured using a Zeiss 510 fluorescent confocal microscope as described in Lattanzio et al, 2005.

Figure 4:
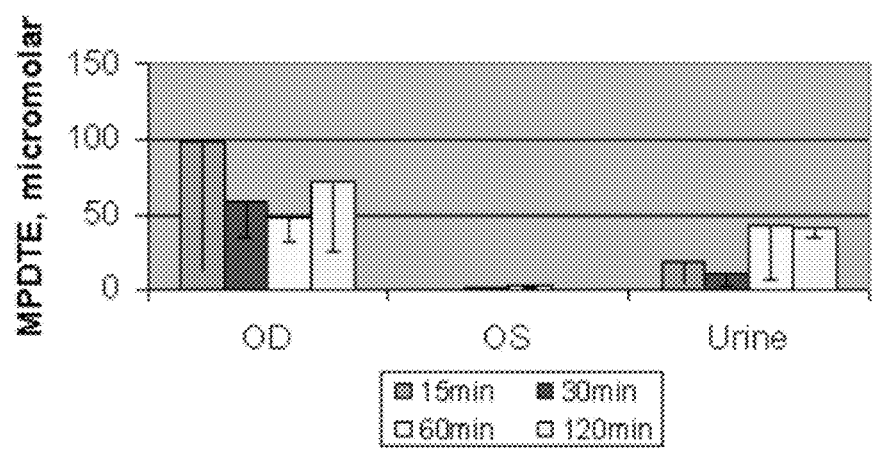
FIG. 4 demonstrates penetration of MPDTE into the globe in rats upon topical ocular administration.

FIG. 4 demonstrates penetration of MP compounds into the globe in rats with topical ocular administration but with very little crossover into the untreated contralateral eye or the brain (brain data not shown). Elimination of MPDTE is primarily through the urine. Chronic topical dosing of normal rats showed no ocular toxicity in either eye as detected in slit lamp or confocal examinations after one month and no residual change in IOP.

Figure 5:
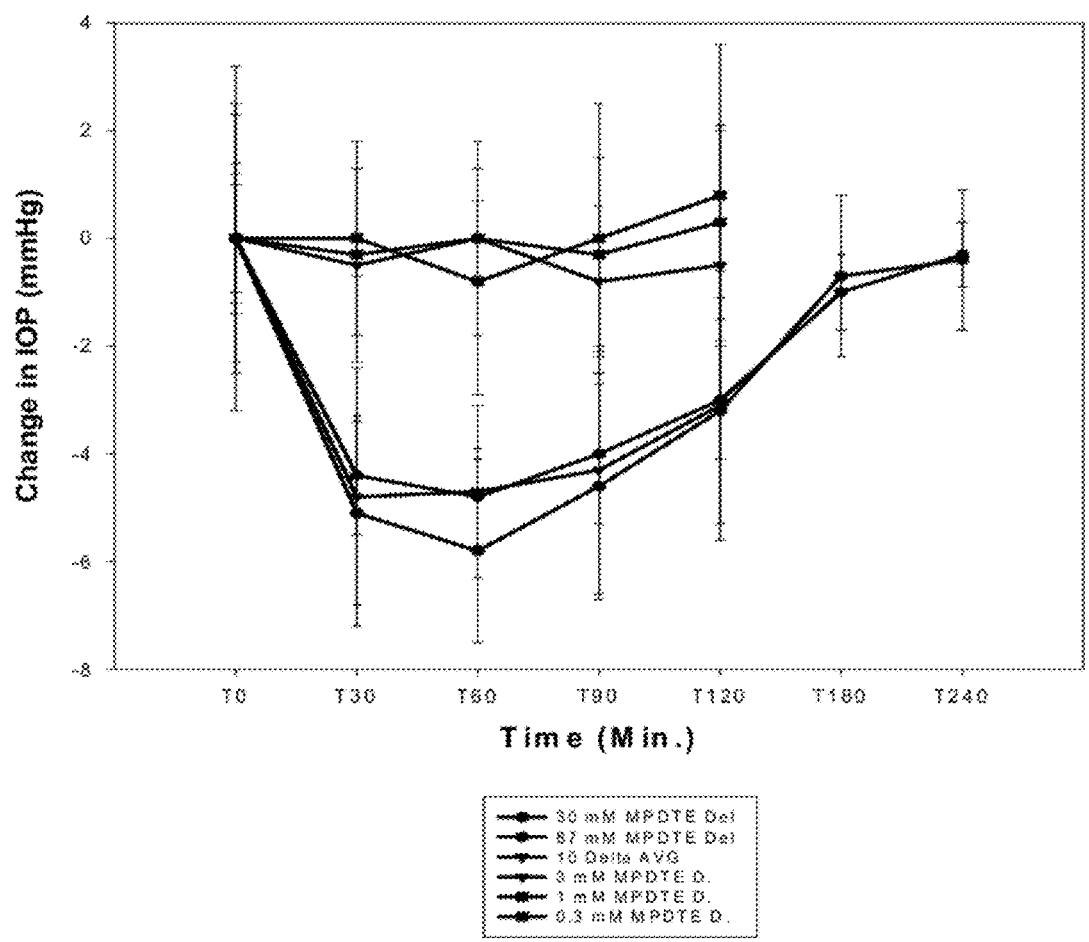
FIG. 5 illustrates the dose response of topical ocular administration of MPDTE.
Figure 6:
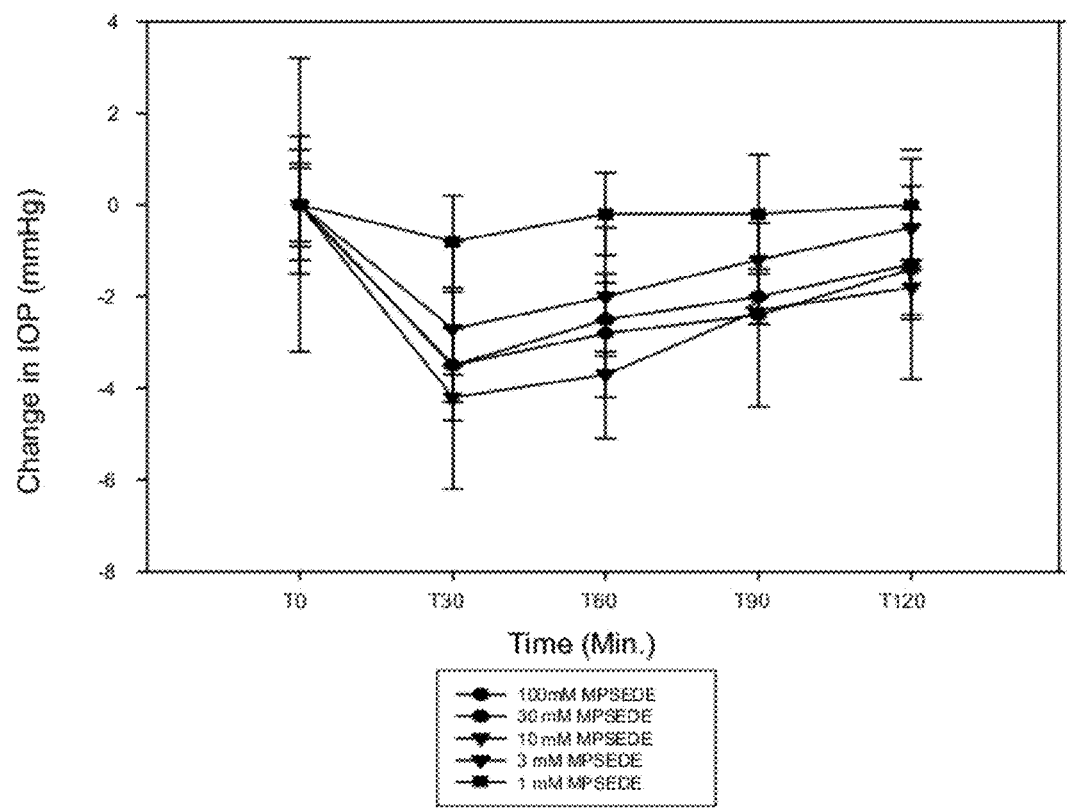
FIG. 6 illustrates the dose response of topical ocular administration of MPSEDE.
Figure 7:
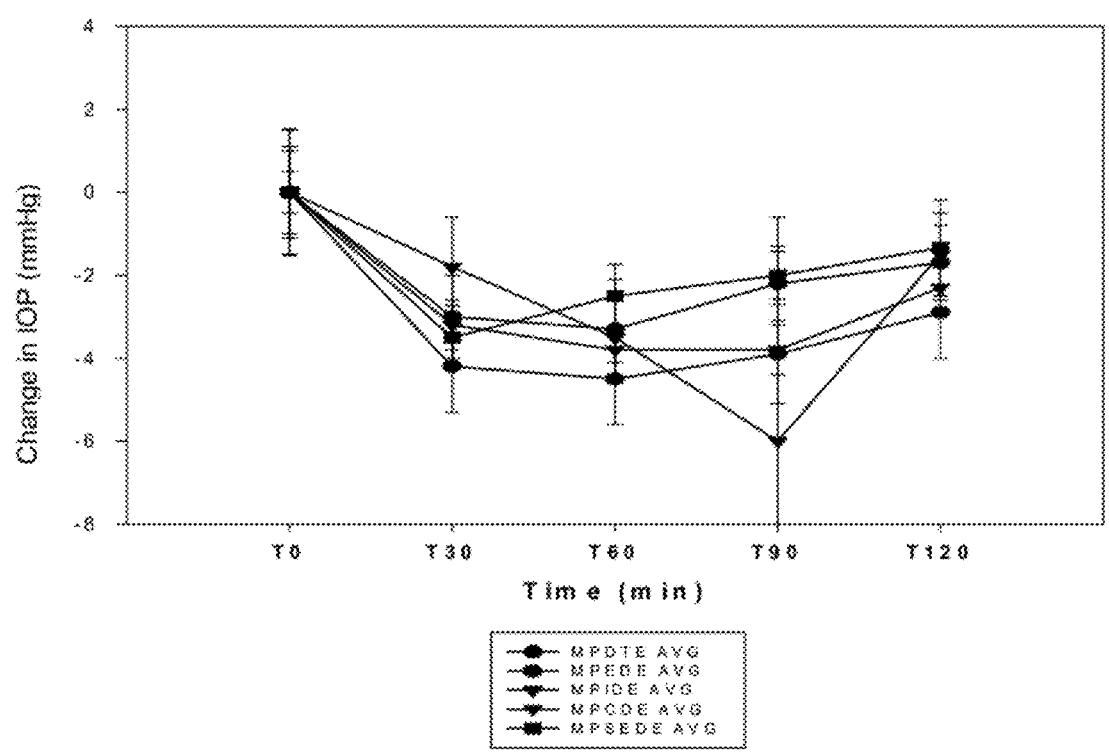
FIG. 7 illustrates the average dose response of topical ocular administration of 30 mM MP compounds.
Figure 8:
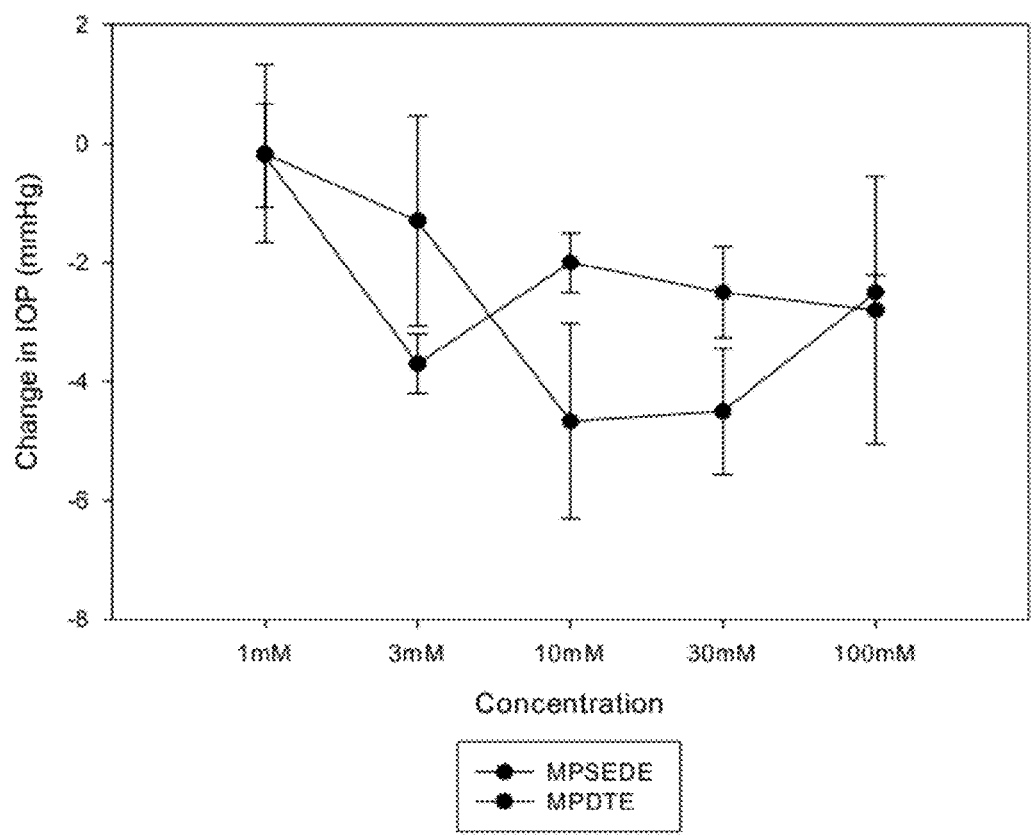
FIG. 8 illustrates the effect of increasing concentration of MPSEDE and MPDTE on intraocular pressure.
Figure 9:
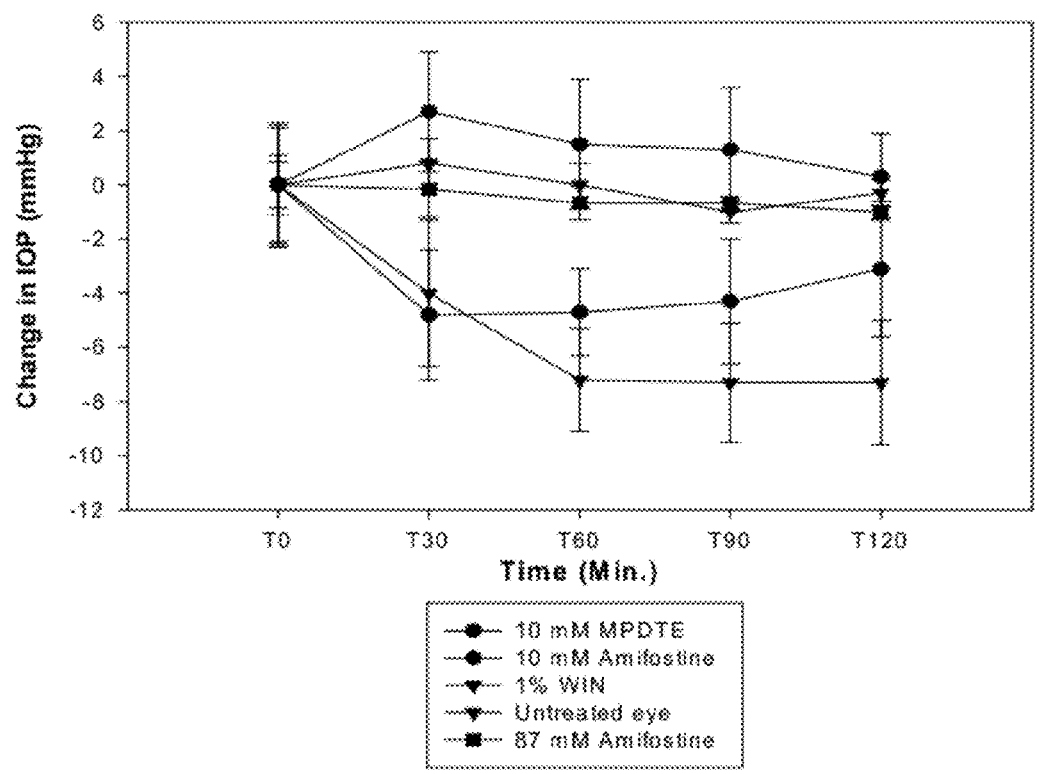
FIG. 9 illustrates comparison of the IOP reduction caused by MPDTE with known radioprotectant.

Initial testing of MPDTE and MPSEDE demonstrated that a single dose of 10-100 mM significantly reduced IOP (FIG. 5, FIG. 6, FIG. 7). The MPDTE and MPSEDE dose-response curve at 60 minutes, near the peak of most of the topical MP IOP responses, is shown in FIG. 8. The IOP reduction caused by MPDTE could be maintained for ~2 hours with a single dose and is compared with the experimental cannabinoid (1% WIN 55,212-2) or amifostine in FIG. 9. No reduction in IOP was seen with 10 mM or 87 mM amifostine.

Figure 10:
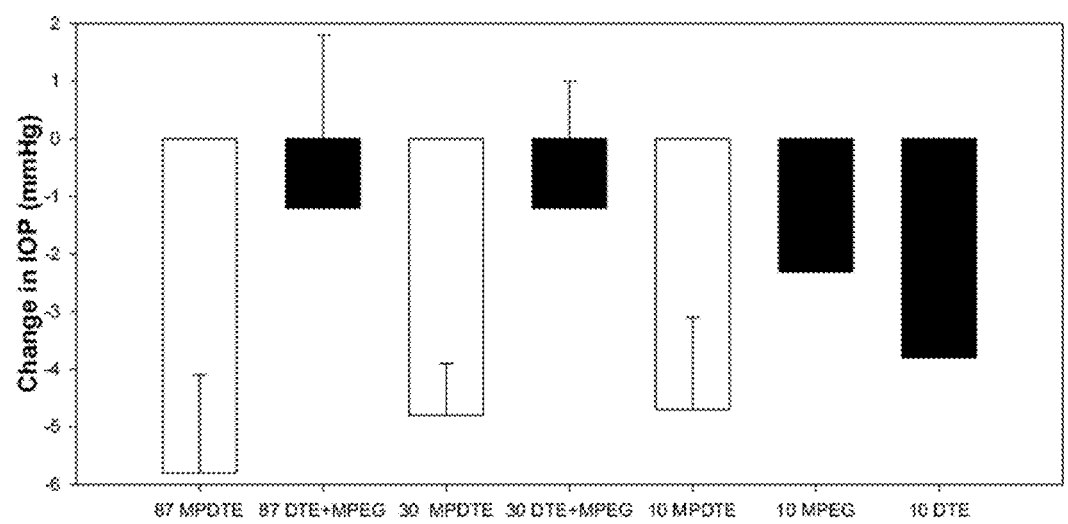
FIG. 10 illustrates comparison of the IOP reduction caused by MPDTE, MP, and DTE.

The mechanism of reduction in IOP was explored by comparing the individual and combined effects of the MP backbone and the effects of the chelator group DTE. As seen in FIG. 10, there is a reduction in IOP when either MP or DTE is administered alone or together, but the IOP reduction was not as great as with MPDTE.

Figure 11:
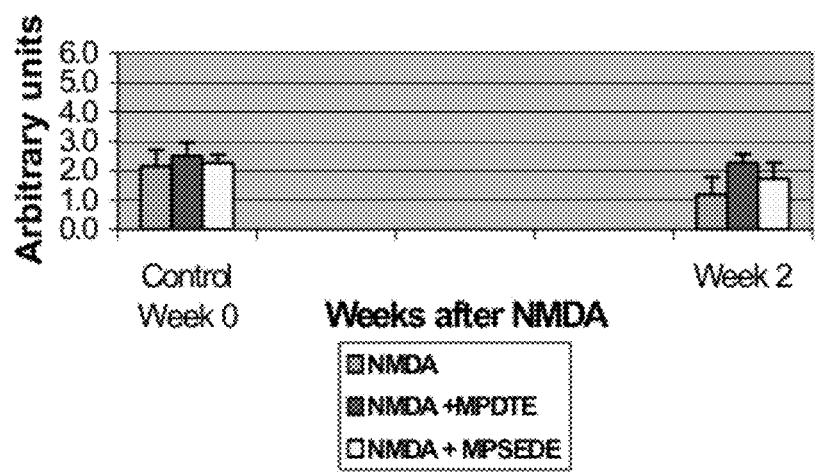
FIG. 11 illustrates a representative A-Wave component of electroretinogram measurements following co-administration of MP compounds with NMDA.
Figure 12:
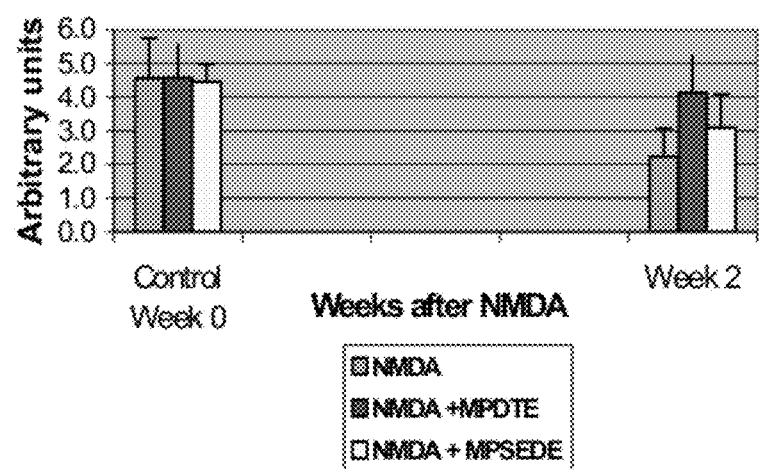
FIG. 12 illustrates a representative B-Wave component of electroretinogram measurements following co-administration of MPG compounds with NMDA.

Co-administration of MPDTE with NMDA significantly maintained A-wave (FIG. 11) and B-wave (FIG. 12) amplitudes, respectively, in comparison to the reductions seen with NMDA alone. MPSEDE showed a trend to reduce NMDA damage, but this was not significant at the dose tested. Both intravitreal and topical administration of either MPSEDE or MPDTE significantly reduced NMDA damage (Table 1).

TABLE 1

| % Baseline | Intravitreal A/B wave | Topical A/B wave |
| --- | --- | --- |
| NMDA | 51.2/68.4 | 51.2/68.4 |
| NMDA + MPDTE | 90.0/90.0 | 82.5/88.1 |
| NMDA + MPSEDE | 76.2/69.6 | 95.9/93.7 |
| NMDA + Amifostine | 94.2/83.3 | 69.4/99.3 |

Chemoprotection

H9C2 cells, a rat myocyte model, were cultured in MEM until confluent using techniques described in Lattanzio et al, 2005. The cells were treated with 5 µM fluo-3 AM, a fluorescent calcium indicator, for 30 min at 37 C, washed and then exposed to 50 µM doxorubicin (a supermaximal toxic dose), in the presence or absence of 30 min pretreatment with 2 mM MPDTE. Doxorubicin increases intracellular calcium in cardiac cells by disrupting calcium homeostasis through the production of free radical damage and subsequent membrane damage. After a 10 min exposure intracellular calcium increased 59.4% in untreated cells, but only 40.2% in MPDTE treated cells ($p<0.001$ for $n=20$ cells in 3 separate trials). Protection may have occurred due to a combination of free radical scavenging and calcium chelation.

From the foregoing description, one skilled in the art can easily ascertain the essential characteristics of the present invention and, without departing from the spirit and scope thereof, can make various changes and modifications of the invention to adapt it to various usages and conditions.

We claim:

1. A method for preventing retinal cell death resulting from glaucoma in a patient in need thereof comprising administering to the patient a therapeutically effective amount of a composition comprising a methoxypolyethylene glycol ester of diethylenetriaminepentaacetic acid.

2. The method of claim 1, wherein the composition is administered topically.

3. The method of claim 1, wherein the composition is administered intravitreally.

4. The method of claim 1, wherein the composition further comprises at least one pharmaceutically acceptable carrier or a pharmaceutically acceptable adjuvant.

5. A method of reducing intraocular pressure in a patient comprising administering to the patient a composition comprising an effective amount of a methoxypolyethylene glycol ester of diethylenetriaminepentaacetic acid.

6. The method of claim 5, wherein the composition is administered topically.

7. The method of claim 5, wherein the composition is administered intravitreally.

8. The method of claim 5, wherein the composition further comprises at least one pharmaceutically acceptable carrier or a pharmaceutically acceptable adjuvant.

\* \* \* \* \*